(12) United States Patent
Hille

(10) Patent No.: US 8,055,722 B2
(45) Date of Patent: Nov. 8, 2011

(54) NOTIFICATION CONTROL THROUGH BRAIN MONITORING OF END USER CONCENTRATION

(75) Inventor: Dale R. Hille, Raleigh, NC (US)

(73) Assignee: International Business Machines Corporation, Armonk, NY (US)

( * ) Notice: Subject to any disclaimer, the term of this patent is extended or adjusted under 35 U.S.C. 154(b) by 29 days.

(21) Appl. No.: 12/629,734

(22) Filed: Dec. 2, 2009

(65) Prior Publication Data

US 2011/0131274 A1    Jun. 2, 2011

(51) Int. Cl.
*G06F 15/16*    (2006.01)
(52) U.S. Cl. .................. 709/207; 709/206; 600/544
(58) Field of Classification Search .......... 709/206, 709/207, 204; 600/410, 544, 586; 607/45; 604/503; 701/9
See application file for complete search history.

(56) References Cited

U.S. PATENT DOCUMENTS

| | | | |
|---|---|---|---|
| 2006/0064037 A1* | 3/2006 | Shalon et al. | 600/586 |
| 2007/0010795 A1* | 1/2007 | Sarkela et al. | 604/503 |
| 2007/0167991 A1* | 7/2007 | DiLorenzo | 607/45 |
| 2008/0177197 A1 | 7/2008 | Lee et al. | |
| 2009/0024050 A1* | 1/2009 | Jung et al. | 600/544 |
| 2009/0112077 A1 | 4/2009 | Nguyen et al. | |
| 2010/0069739 A1* | 3/2010 | decharms | 600/410 |
| 2011/0029162 A1* | 2/2011 | Ishihara et al. | 701/9 |

OTHER PUBLICATIONS

Al Fin; "Smarter Brain Monitoring", May 26, 2009; http://alfin2100.blogspot.com/2009/05/smarter-brain-monitoring/html; Last visited on Nov. 4, 2009.
Melissa Perenson; "Oddball Gadget: Mattel Mind Flex"; Jan. 10, 2009; http://www.pcworld.com/article/156860/oddball_gadget_mattel_mind_flex.html; Last visited on Dec. 2, 2009.
Joshua Fruhlinger; "Brains-on with Neuro-Sky and Square Enix's Judecca mind-control game"; Oct. 9, 2008; http://www.engadget.com/2008/10/09/brains-on-with-neurosky-and-squareenixs-judecca-mind-control-ga/; Last visited on Dec. 2, 2009.
Mike Snider; "Toy trains 'Star Wars' fans to use the Force"; Jan. 7, 2009; http://www.usatoday.com/life/lifestyle/2009-01-06-force-trainer-toy_N.htm; Last Visited on Dec. 2, 2009.
Wikipedia; "Electroencephalography"; http://en.wikipedia.org/wiki/Electroencephalography; Last visited on Dec. 2, 2009.

* cited by examiner

*Primary Examiner* — Le Luu
(74) *Attorney, Agent, or Firm* — Steven M. Greenberg, Esq.; Carey, Rodriguez, Greenberg & Paul

(57) ABSTRACT

Embodiments of the present invention provide a method, system and computer program product for message notification management through brain monitoring of end user concentration. In an embodiment of the invention, a method for message notification management through brain monitoring of end user concentration can include receiving neurofeedback for an end user through an interface for a brain monitoring system, comparing the neurofeedback to a threshold level of brain activity indicating a degree of concentration of the end user, and suppressing message notifications for messages in a messaging system responsive to the neurofeedback exceeding the threshold level of brain activity, but otherwise permitting message notifications for messages in the messaging system.

19 Claims, 1 Drawing Sheet

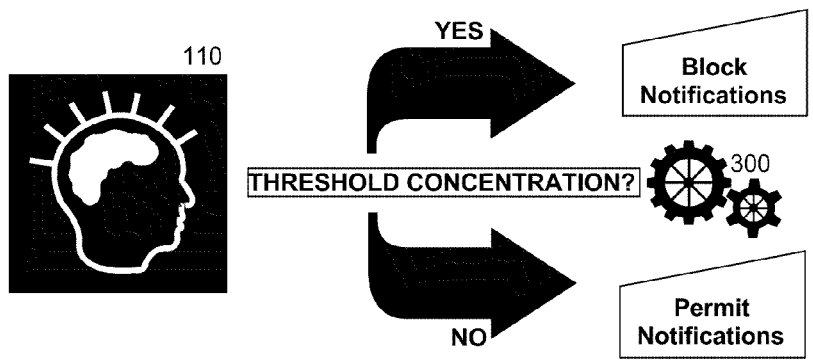
FIG. 1
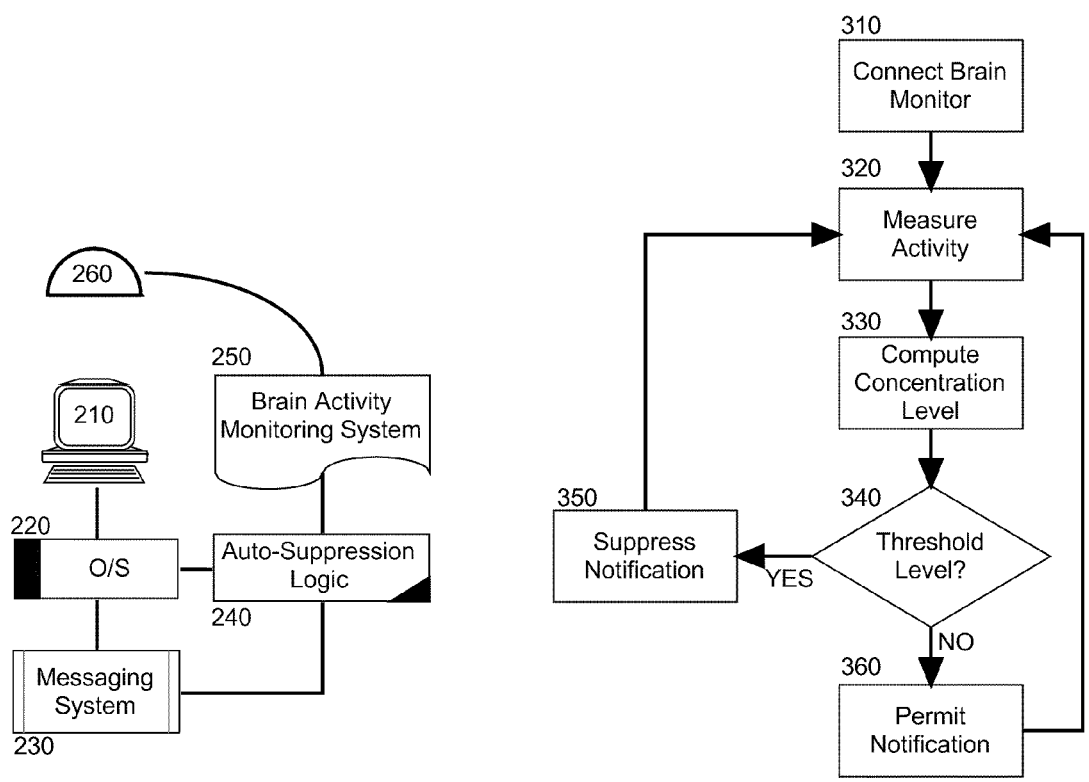
FIG. 2
FIG. 3

NOTIFICATION CONTROL THROUGH BRAIN MONITORING OF END USER CONCENTRATION

BACKGROUND OF THE INVENTION

1. Field of the Invention

The present invention relates to electronic messaging systems and more particularly to notification systems for incoming messages in an electronic messaging system.

2. Description of the Related Art

Electronic messaging represents the single most useful task accomplished over wide-scale computer communications networks. Some argue that in the absence of electronic messaging, the Internet would have amounted to little more than a science experiment. Today, electronic messaging seems to have replaced the ubiquitous telephone and fax machine for the most routine of interpersonal communications. As such, a variety of electronic messaging systems have arisen which range from real-time instant messaging systems and wireless text pagers to asynchronous electronic mail systems.

Electronic mail, a form of electronic messaging referred to in the art as e-mail, has proven to be the most widely used computing application globally. Though e-mail has been a commercial staple for several decades, due to the explosive popularity and global connectivity of the Internet, e-mail has become the preferred mode of communications, regardless of the geographic separation of communicating parties. Today, more e-mails are processed in a single hour than phone calls. Clearly, e-mail as a mode of communications has been postured to replace all other modes of communications save for voice telephony.

In the early days of computing, few participated in electronic messaging such that one could ascertain the presence of a new message simply by inspecting a directory of incoming messages. As the popularity of electronic messaging has grown over the years, however, notification systems have arisen to provide both audible and visual notifications when a new electronic message has been received. Importantly, the explosive use of electronic messaging systems has resulted in entirely separate applications having the sole purpose of managing the notification duties of an electronic messaging system.

For many computing users of electronic messaging systems, the volume of electronic messages received daily can be unmanageable and often can result in the recipient of a volume of electronic messages becoming overwhelmed. While in the past electronic messaging notification systems alerted end users to the receipt of a message, the frequent receipt of messages and resulting repetitive notifications can become irritating to the end user. In fact, oftentimes end users simply disable the notification system because there is nary a chance to review all incoming messages at once to determine which are important and which can be ignored for the time being. To do so, however, can cause important messages to go unnoticed.

BRIEF SUMMARY OF THE INVENTION

Embodiments of the present invention address deficiencies of the art in respect to message management and provide a novel and non-obvious method, system and computer program product for message notification management through brain monitoring of end user concentration. In an embodiment of the invention, a method for message notification management through brain monitoring of end user concentration can include receiving neurofeedback for an end user through an interface for a brain monitoring system, comparing the neurofeedback to a threshold level of brain activity indicating a degree of concentration of the end user, and suppressing message notifications for messages in a messaging system responsive to the neurofeedback exceeding the threshold level of brain activity, but otherwise permitting message notifications for messages in the messaging system.

In another embodiment of the invention, a messaging data processing system can include a messaging system executing in memory by a processor of a host computing device, a brain activity monitoring system coupled to the messaging system, and message suppression logic coupled to the messaging system and the brain activity monitoring system. The logic can include program code that when executed by the processor compares neurofeedback received from the brain activity monitoring system to a threshold level of brain activity indicating a degree of concentration and suppresses message notifications for messages in a messaging system responsive to the neurofeedback exceeding the threshold level of brain activity, but otherwise permits message notifications for messages in the messaging system.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 1 is a pictorial illustration of a process for message notification suppression through brain monitoring of end user concentration;

FIG. 2 is a messaging data processing system configured for message notification suppression through brain monitoring of end user concentration; and, FIG. 3 is a method for message notification suppression through brain monitoring of end user concentration.

DETAILED DESCRIPTION OF THE INVENTION

Embodiments of the invention provide for message notification suppression through brain monitoring of end user concentration. In accordance with an embodiment of the invention, brain activity of an end user interacting with a computing device can be monitored to identify a recognizable state of concentration. In response to detecting a threshold state of concentration in the end user, notifications for a messaging system executing in the computing device can be suppressed when received. Optionally, a presence awareness status of the end user can be changed to indicate unavailability of the end user in response to detecting the threshold state of concentration. Once it is determined that a state of concentration of the end user has returned to a lower threshold state of concentration, message notifications received in the messaging system are no longer suppressed and, optionally, the presence awareness status of the end user can be changed to reflect the availability of the end user.

In further illustration, FIG. 1 is a pictorial illustration of a process for message notification suppression through brain monitoring of end user concentration. As shown in FIG. 1, an end user 110 can be configured for brain activity monitoring. Exemplary technologies can include an electroencephalography (EEG) headset providing as neurofeedback, quantified levels of alertness for an end user wearing a sensor laden data acquisition headset. A process for the automated suppression of notifications 300 in a messaging system, in response to the measurement of brain activity for the end user 110, can compute a level of concentration of the end user 110 and can compare the computed level of concentration to a threshold level. The messaging system itself can include, by way of example, an e-mail messaging system, an instant messaging system, a voice mail messaging system, an incoming call alert system or even a text messaging system.

To the extent the measured level of concentration of the end user 110 exceeds the threshold level, the process for the automated suppression of notifications 300 can suppress or otherwise block notifications of incoming messages in the messaging system so as to not disturb the high degree of concentration experienced by the end user. Conversely, to the extent the measured level of concentration of the end user 110 does not exceed the threshold level, the process for the automated suppression of notifications 300 can permit notifications of incoming messages in the messaging system. Optionally, the process for the automated suppression of notifications 300 can modify a presence awareness status of the end user 110 to indicate when the end user 110 experiences a high degree of concentration so as to dissuade others from interrupting the end user 110 with a message.

The process described in connection with FIG. 1 can be deployed in a messaging data processing system. In further illustration, FIG. 2 is a messaging data processing system configured for message notification suppression through brain monitoring of end user concentration. The system can include a host computing device 210 with processor and memory, for example a personal computer, a PDA, a smart mobile phone (cellular telephone), and the like. The host computing device 210 can support the execution of an operating system 220 hosting the operation of a messaging system 230, such as an e-mail messaging client, an instant messaging client, a text messaging client, or a voice mail system, to name a few.

Of note, auto-suppression logic 240 can be coupled to both the messaging system 230 and to a brain activity monitoring system 250 including a remote sensor array 260. As an example, the activity monitoring system 250 can include an EEG headset with companion data acquisition system and data reduction system configured to output neurofeedback data received through the EEG headset at the command of the data acquisition system and processed into a quantified level of alertness by the data reduction system. The auto-suppression logic 240 can include program code that when executed in the memory by the processor of the host computing device 210, can determine whether a measured level of concentration by the brain activity monitoring system 250 exceeds a threshold level representative of a high concentration level. The program code when executed further can suppress notifications of received messages in the messaging system 230 responsive to determining that the measured level of concentration exceeds the threshold.

In even yet further illustration of the operation of the auto-suppression logic 240, FIG. 3 is a flow chart illustrating a method for message notification suppression through brain monitoring of end user concentration. The process can begin in block 310 with the establishment of a communicative link to a brain activity monitoring system. In block 320, brain activity for an end user can be measured and in block 330, a concentration level of the brain activity can be computed. In decision block 340, if the computed concentration level exceeds a threshold level, then in block 350 subsequent notifications for received messages can be suppressed or blocked. Otherwise, in block 360 subsequent notifications for received messages can be permitted.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, radiofrequency, and the like, or any suitable combination of the foregoing. Computer program code for carrying out operations for aspects of the present invention may be written in any combination of one or more programming languages, including an object oriented programming language and conventional procedural programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention have been described above with reference to flowchart illustrations and/or block diagrams of methods, apparatus (systems) and computer program products according to embodiments of the invention. In this regard, the flowchart and block diagrams in the Figures illustrate the architecture, functionality, and operation of possible implementations of systems, methods and computer program products according to various embodiments of the present invention. For instance, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It also will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

I claim:

1. A method for message notification management through brain monitoring of end user concentration, the method comprising:
   receiving neurofeedback for an end user through an interface for a brain monitoring system;
   comparing the neurofeedback to a threshold level of brain activity indicating a degree of concentration of the end user; and,
   suppressing message notifications for messages in a messaging system responsive to the neurofeedback exceeding the threshold level of brain activity, but otherwise permitting message notifications for messages in the messaging system.

2. The method of claim 1, wherein the brain activity monitoring system is an electroencephalography (EEG) based brain activity monitoring system.

3. The method of claim 1, wherein the messaging system is an e-mail messaging system.

4. The method of claim 1, wherein the messaging system is an instant messaging system.

5. The method of claim 1, wherein the messaging system is a text messaging system.

6. The method of claim 1, wherein the messaging system is a voice mail messaging system.

7. A messaging data processing system comprising:
   a messaging system executing in memory by a processor of a host computing device;
   a brain activity monitoring system coupled to the messaging system; and,
   message suppression logic coupled to the messaging system and the brain activity monitoring system, the logic comprising program code that when executed by the processor compares neurofeedback received from the brain activity monitoring system to a threshold level of brain activity indicating a degree of concentration and suppresses message notifications for messages in a messaging system responsive to the neurofeedback exceeding the threshold level of brain activity, but otherwise permits message notifications for messages in the messaging system.

8. The system of claim 7, wherein the brain activity monitoring system is an electroencephalography (EEG) based brain activity monitoring system.

9. The system of claim 7, wherein the messaging system is an e-mail messaging system.

10. The system of claim 7, wherein the messaging system is an instant messaging system.

11. The system of claim 7, wherein the messaging system is a text messaging system.

12. The system of claim 7, wherein the messaging system is a voice mail messaging system.

13. The system of claim 7, wherein the messaging system is an incoming call alert system.

14. A computer program product comprising a computer usable storage medium storing computer usable program code for message notification management through brain monitoring of end user concentration, the computer program product comprising:

computer usable program code for receiving neurofeedback for an end user through an interface for a brain monitoring system;

computer usable program code for comparing the neurofeedback to a threshold level of brain activity indicating a degree of concentration of the end user; and, computer usable program code for suppressing message notifications for messages in a messaging system responsive to the neurofeedback exceeding the threshold level of brain activity, but otherwise permitting message notifications for messages in the messaging system.

15. The computer program product of claim 14, wherein the brain activity monitoring system is an electroencephalography (EEG) based brain activity monitoring system.

16. The computer program product of claim 14, wherein the messaging system is an e-mail messaging system.

17. The computer program product of claim 14, wherein the messaging system is an instant messaging system.

18. The computer program product of claim 14, wherein the messaging system is a text messaging system.

19. The computer program product of claim 14, wherein the messaging system is a voice mail messaging system.

* * * * *